United States Patent
Forestiere et al.

(10) Patent No.: US 7,160,836 B2
(45) Date of Patent: Jan. 9, 2007

(54) MATERIALS COMPRISING ORGANIC GROUPS CONTAINING SULPHUR AND PHOSPHOROUS BONDED TO A MINERAL OXIDE VIA OXYGEN ATOMS

(75) Inventors: Alain Forestiere, Vernaison (FR); P. Hubert Mutin, Clapiers (FR); Andre Vioux, Montferrier sur Lez (FR); Gilles Guerrero, Beziers (FR)

(73) Assignee: Institut Francois du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 11/200,038

(22) Filed: Aug. 10, 2005

(65) Prior Publication Data

US 2006/0014635 A1 Jan. 19, 2006

Related U.S. Application Data

(63) Continuation of application No. 09/864,877, filed on May 25, 2001, now abandoned.

(30) Foreign Application Priority Data

May 25, 2000 (FR) .................................. 00 06803

(51) Int. Cl.
  *B01J 31/00* (2006.01)
(52) U.S. Cl. ....................................... 502/168; 502/162
(58) Field of Classification Search ................ 502/168, 502/162
  See application file for complete search history.

(56) References Cited

U.S. PATENT DOCUMENTS 3,177,233 A * 4/1965 Calhoun ...................... 556/19
4,994,429 A * 2/1991 Wieserman et al. ......... 502/401
5,616,749 A * 4/1997 Cheng et al. ................ 502/162
6,958,307 B1 * 10/2005 Forestiere et al. .......... 502/162

FOREIGN PATENT DOCUMENTS

FR 2 753 971 * 9/1996

OTHER PUBLICATIONS

G. Alberti et al., Adv. Mater. 1996, vol. 8, No. 4, pp. 291-303.*
M. Dines et al., Inorg. Chem., vol. 20, No. 1, 1981, pp. 92-97.*
XP 000675663—Journal of Molecular Catalysis, "Catalyst design of two-dimensional zirconium phosphonates" By Kohichi Segawa et al., vol. 74, No. 1-03, 1992, pp. 213-221.

* cited by examiner

*Primary Examiner*—Elizabeth D. Wood
*Assistant Examiner*—J. Pasterczyk

(57) ABSTRACT

The invention describes materials comprising organic groups containing sulphur and phosphorous bonded together by a hydrocarbon chain and bonded via phosphorous and oxygen atoms to a mineral oxide of an element M, said materials being characterized in that they comprise M-O-M' bonds, M'representing an element of a mineral oxide identical to or different from M, in that the ratio of the element M to the phosphorous is about 0.5: 1 to about 500:1 and in that each phosphorous atom of the phosphorous-containing groups forms at least one P—O-M bond and/or P—O-M' bond. The invention also describes a process for preparing such materials.

27 Claims, 1 Drawing Sheet

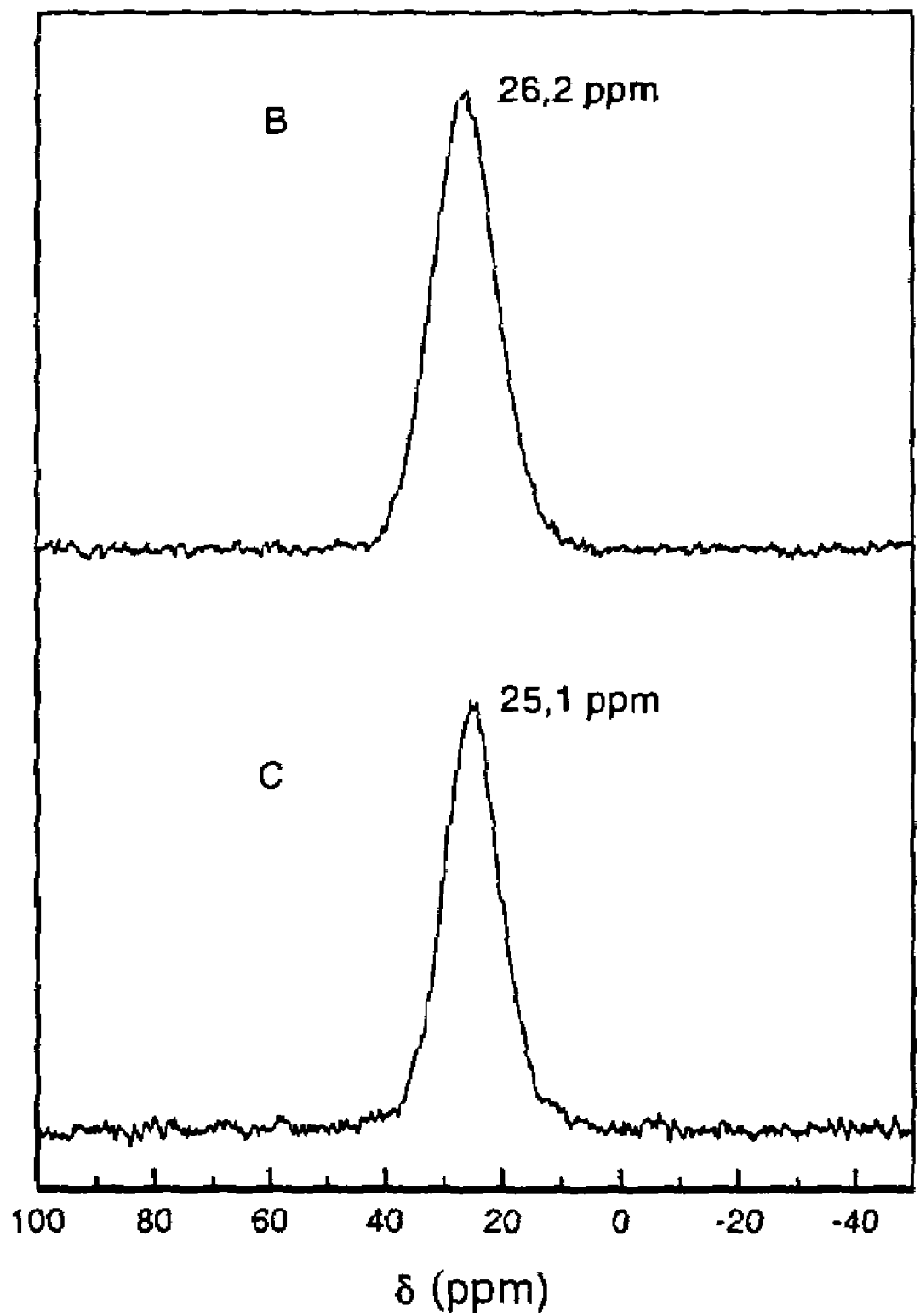

MATERIALS COMPRISING ORGANIC GROUPS CONTAINING SULPHUR AND PHOSPHOROUS BONDED TO A MINERAL OXIDE VIA OXYGEN ATOMS

This application is a continuation of U.S. application Ser. No. 09/864,877 filed May 25, 2001, which is now abandoned.

The present invention relates to materials comprising organic groups containing phosphorous bonded via covalent bonds to a mineral oxide and to another functional terminal group such as a functional group containing sulphur, and to their preparation. It also relates to the applications of said materials in particular in catalysis, especially when the organic sulphur-containing group is a terminal sulphonic group or a sulphonic derivative, and also as an adsorbent or complexing agent, in particular when the organic sulphur-containing group is a terminal thiol group or a thiol group derivative, such as a sulphide or a polysulphide.

Such materials offer an alternative to materials produced by grafting organosilicon groups to mineral oxides or cross-linked polysiloxanes, to heterogenise by grafting on organic functions. The use of phosphorous-containing groups and organophosphorous groups have different advantages over the use of organosilicon groups. The ease of formation and stability of P—O-metal bonds enable mineral oxide matrices other than silica (for example alumina, zirconium dioxide or titanium dioxide) to be used that are more stable chemically. The absence of POH/POH homocondensation reactions under the usual preparation conditions ensures better homogeneity, i.e., the formation of only P—O-metal bonds to the exclusion of P—O—P bonds.

Materials particularly used as an adsorbent obtained by reaction between reactive sites on oxide/hydroxide particles and a phosphorous-containing compound containing one or more organic acid groups have been described, for example, in United States patents U.S. Pat. No. 4,788,176 and U.S. Pat. No. 4,994,429. Those patents teach that such compounds are obtained by grafting the oxides/hydroxides using acidic compounds such as phosphonic or phosphinic acids. Grafting commences at a highly acidic pH, for example 1.8, causing the formation of aluminium phosphonate when the particles are alumina particles. Further, the use of acidic compounds to carry out grafting can lead to the formation of multi-layers, which is not helpful in most applications, particularly catalysis. Only U.S. Pat. No. 4,994,429 provides an example of an aluminium oxide grafted with a functional group containing sulphur in the form of a sulphonic group that is introduced by reacting the mineral solid, grafted using phenyl-phosphonic acid, with fuming sulphuric acid, i.e., containing sulphuric anhydride, a highly acidic medium with a non negligible risk of attack by alumina.

We have now discovered a functionalised solid and a method for preparation by gel formation from molecular precursors of this solid that can overcome the disadvantages of the prior art preparation method and introduce the desired functionality either before or after the gel formation step.

In its broadest aspect, the functionalised solid of the present invention is defined as a material comprising organic groups containing sulphur and phosphorous bonded together by a hydrocarbon chain and bonded via phosphorous and oxygen atoms to a mineral oxide of one or more elements M, said materials being characterized in that they comprise M-O-M' bonds, M' representing an element of a mineral oxide identical to or different from M, in that the ratio of element M to the phosphorous is about 0.5:1 to about 500:1 and in that each phosphorous atom of the phosphorous-containing groups forms at least one P—O-M bond and/or P—O-M' bond.

In a particular embodiment, the material of the present invention is a material in which M and M' represent the same element. The ratio of element M to the phosphorous is usually about 0.5:1 to about 150:1, preferably about 0.5:1 to about 20:1. The sulphur to phosphorous ratio is normally about 0.05:1 to about 10:1, normally about 0.1:1 to about 5:1 and usually about 0.4:1 to about 2:1.

The material of the present invention is normally a material in which M and M' represent an element from groups IB, IIB, IIIB, IVB, VB, VIB, VIIB, VIII, IIIA, IVA, the lanthanides or the actinides of the periodic table; usually, M and M' represent an element selected from the group formed by titanium, zirconium, iron, aluminium, silicon and tin, and preferably selected from elements from the group formed by titanium, zirconium and aluminium.

The organic sulphur-containing group is preferably selected from thiol groups and their derivatives, and from sulphonic acid groups and their derivatives.

The phosphorous-containing groups are normally groups of the phosphate, phosphonate or phosphinate types shown below:

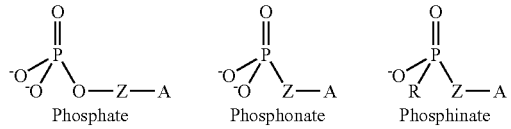

Phosphate    Phosphonate    Phosphinate

EXAMPLES OF PHOSPHOROUS-CONTAINING GROUPS

In the above, A represents the organic sulphur-containing group and Z is a hydrocarbon group that will be defined below in connection with the process for preparing the materials of the present invention.

The invention also concerns a process for preparing a material as defined above, in which at least one phosphorous-containing compound with formula I defined below (optionally in solution in a solvent) is brought into contact with at least one mineral oxide precursor that may be an alkoxylated derivative with formula $M(OR')_z$ or a halogenated derivative with formula $M(Hal)_z$, where z is equal to the valency of element M defined above, Hal is a halogen atom, for example a chlorine or bromine atom, and R' is a hydrocarbon group or another compound of element M (carboxylate, sulphate, nitrate, hydroxide or oxychloride, for example). Usually, at least one precursor is used selected from the group formed by alkoxylated derivatives with formula $M(OR')_z$ and halogenated derivatives with formula $M(Hal)_z$ where z is equal to the valency of the element M defined above, Hal is a halogen atom, for example a chlorine or bromine atom, and R' is a hydrocarbon group usually containing 1 to 12 carbon atoms.

The formula for the phosphorous-containing compounds can be written as follows:

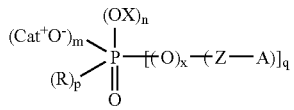

where the sum m+n+p+q is equal to 3, m=0, 1 or 2, q=0, 1 or 2, x=0 or 1, p=0, 1 or 2, R is a hydrocarbon group, X is a hydrocarbon group or a group with formula $SiR''_3$ where R'' is a hydrocarbon group, Z is a hydrocarbon group optionally including heteroatoms, $Cat^+$ is a monovalent cation and A is a sulphur-containing group or a reactive group that can be transformed into a sulphur-containing group.

Usually, an alkoxylated derivative with formula $M(OR')_z$, where R' is an alkyl group containing 1 to 12 carbon atoms, preferably 1 to 6 carbon atoms, is brought into contact with a solution in a solvent of a phosphorous-containing compound with formula I where $Cat^+$ is a proton $H^+$, R is an alkyl group containing 1 to 18 carbon atoms or an aryl group containing 6 to 18 carbon atoms or an alkyl-aryl group containing 7 to 24 carbon atoms, X is a group with formula $SiR''_3$, where R'' is a hydrocarbon group containing 1 to 18 carbon atoms, for example, or an aryl group containing 6 to 18 carbon atoms, for example, or an alkyl-aryl group containing 7 to 24 carbon atoms, for example, Z is a saturated or unsaturated bivalent alkyl group containing 1 to 18 carbon atoms or a bivalent aryl group containing 6 to 18 carbon atoms or a bivalent alkyl-aryl or aryl-alkyl group containing 7 to 24 carbon atoms and A is a sulphur-containing group selected from thiols and their derivatives and sulphonic acids and their derivatives. This group A is preferably a thiol group with formula —SH or a sulphonic group with formula $—SO_3^-Cat'^+$ where $Cat'^+$ represents a proton $H^+$ or a monovalent cation such as an alkali metal cation. Group A can also be a reactive group that is transformable into a sulphur-containing group, usually a halogenated group.

The phosphorous-containing group with formula I is preferably a compound with formula I where m=2, q=1 and n=p=zero or a compound with formula I where n=2, q=1 and m=p=zero. Formation of the functionalised solid of the invention can be described as resulting from the formation of M-O—P or M'-O—P bonds by condensation of P—OX or P—$O^-Cat^+$ functions of the phosphorous-containing compound with functions of the derivative of element M or M' and by complexing the phosphoryl group with the element M, and from the formation of M-O-M or M'-O-M bonds by hydrolysis-condensation of functions of element M or M'.

The preferred phosphorous-containing compound with formula I is a compound in which Z is a saturated bivalent alkyl group containing 1 to 6 carbon atoms, preferably a polymethylene group, and usually a polymethylene group containing 1 to 4 carbon atoms. The solvent for the phosphorous-containing compound with formula I is, for example, an organic solvent such as tetrahydrofuran, dimethylsulphoxide or dichloromethane, or a mineral solvent such as water. The scope of the present invention also encompasses the use of a mixture of at least two solvents.

The various steps for preparing the materials of the present invention are individually conventional steps that are well known to the skilled person; references will be made to those steps in the following examples that illustrate the invention without limiting its scope.

EXAMPLE 1

In this example, a functionalised solid was prepared containing a bromo group that was then transformed into a functionalised solid containing a thiol group.

In a first step, the Arbuzov reaction (J. March, Advanced Organic Chemistry, $3^{rd}$ Edition, John Wiley & Sons, New York, 1985, p. 848) was used to prepare a phosphonate with formula $Br(CH_2)_3PO_3Et_2$ (I'). The second step of this preparation was hydrolysis of the P—OEt bonds to a P—OH bond that produced phosphonic acid with formula $Br(CH_2)_3PO_3H_2$ (I).

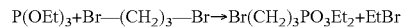

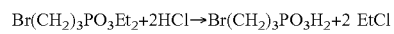

1 equivalent of triethylphosphite and 1.5 equivalents of 1,3-dibromopropane were introduced into a reactor in a nitrogen atmosphere. The reactor was heated to 140° C. and held at that temperature, with stirring, for 24 h. After distilling at a pressure of 0.1 millibars (mbar) (10 pascals) at an average column bottom temperature of 90° C., diethylbromopropylphosphonate with formula $Br(CH_2)_3PO_3Et_2$ (I') was obtained in a yield of 60 mole % with respect to the triethylphosphite introduced. This compound with formula (I') was then heated under reflux for 24 hours in concentrated hydrochloric acid (HCl) then after evaporation at a pressure of 10 mbar at a temperature of 90° C. for 1 hour. Re-crystallisation from acetonitrile produced the phosphonic acid with formula $Br(CH_2)_3PO_3H_2$ (I) was obtained.

2.028 g, i.e., 0.01 moles, of the phosphonic acid with formula (I), $Br(CH_2)_3PO_3H_2$, dissolved in 15 millilitres (ml) of dry tetrahydrofuran (THF) was introduced into a reactor at ambient temperature, then 0.03 moles, i.e., 8.53 g, of tetraisopropoxytitanate with formula $Ti(O^iPr)_4$ was introduced in a nitrogen atmosphere, with stirring. 0.05 moles, i.e., 0.9 g of water diluted in 10 ml of THF was then added dropwise. After stirring for 2 hours at ambient temperature, the solid obtained was washed successively with THF, methanol then acetone. This solid was then dried at a pressure of 0.05 mbar at 100° C. for 5 hours to produce a solid A. Solid A was then functionalised using the procedure given below using a conventional reaction for replacing a halogen atom by a thiol atom described in the book by J. March, Advanced Organic Chemistry, $3^{rd}$ Edition, John Wiley & Sons, New York, 1985, p. 360. 1.3 g of solid gel A was added to 0.56 g, i.e., 10 millimoles, of sodium hydrosulphide in solution in 25 ml of methanol in a reactor. This was then heated under reflux for 10 hours in a nitrogen atmosphere. After filtering, a solid was recovered that was washed successively with methanol, water and acetone. The solid was then dried at a pressure of 0.05 mbars at 100° C. for 5 hours to produce a solid B.

Elemental analysis of solid B gave the following results: Ti, 31.9%; P, 6.1%; S, 4.4%; Br, less than 0.1%. The Ti/P ratio was 3.4 and the S/P ratio was 0.7.

The phosphorous-31 NMR spectrum of solid B (see FIG. 1) carried out using a 300 MHz Bruker Avance apparatus showed a broad peak at 26.2 ppm corresponding to phosphonate groups bonded to titanium atoms; the carbon-13 NMR spectrum of solid B, carried out using a 300 MHz Bruker Avance apparatus, showed three peaks at 25.9 ppm, 22.2 ppm and 39.3 ppm, corresponding to three methylene groups in the P—$CH_2$—$CH_2$—$CH_2$—S concatenation.

EXAMPLE 2

In this example, a functionalised solid containing a sulphonic acid group was prepared.

In a first step, the phosphonate with formula $Br(CH_2)_3PO_3Et_2$ (I') was prepared using the procedure described above. This phosphonate was then functionalised using the procedure given below using a conventional reaction for replacing a halogen atom by a sulphonate group as described in the book by J. March, Advanced Organic Chemistry, 3$^{rd}$ Edition, John Wiley & Sons, New York, 1985, p. 363, to obtain the phosphonate with formula $NaSO_3(CH_2)_3PO_3Et_2$ (II). The last step of this preparation was hydrolysis of the P—OEt bonds to a P—OH bond to produce the phosphonic acid with formula $HSO_3(CH_2)_3PO_3H_2$ (II').

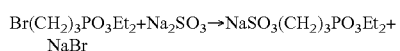

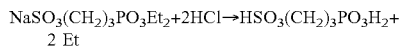

0.1 equivalents (25.91 g) of diethyl bromopropylphosphonate $Br(CH_2)_3PO_3Et_2$ (I') was added to a boiling solution of 0.13 equivalents (12.61 g) of sodium sulphite $NaSO_3$ in 50 ml of water in a reactor in a nitrogen atmosphere. After refluxing for 1 hour, the solution was cooled then eluted through a Dowex 50W-X8 (H+) resin. After evaporation under reduced pressure (15 mbar) at 100° C., an oil was obtained which was refluxed for 24 hours in concentrated hydrochloric acid (HCl) (32% by weight). After evaporation under reduced pressure (15 mbar) at 100° C., a viscous liquid was obtained. This liquid was taken up in 250 ml of boiling water. The solution obtained was eluted through Dowex 50W-XB (H$^+$) resin. The precipitate obtained was filtered, then taken up in 250 ml of water and concentrated hydrochloric acid was added to dissolve it. The solution obtained was eluted through a Dowex 50W-X8 (H$^+$) resin. After evaporation under reduced pressure (10 mbar) at 90° C. then under reduced pressure (0.05 mbar) at 90° C. for 15 hours, a phosphonic acid with formula $HSO_3(CH_2)_3PO_3H_2$ (II'') was obtained.

1.56 g, i.e., 0.01 moles, of phosphonic acid with formula $HSO_3(CH_2)_3PO_3H_2$ (II'') dissolved in 25 millilitres (ml) of dimethylsulphoxide (DMSO) was introduced into a reactor at ambient temperature then 0.05 moles, i.e., 14.21 g of tetraisopropoxytitanate with formula $Ti(O^iPr)_4$ was added, with stirring and in a nitrogen atmosphere. 0.1 moles, i.e., 1.8 g of water diluted in 15 ml of THF was then added dropwise.

After stirring for 2 hours at ambient temperature, a solid was isolated by filtering and washed successively with THF, methanol, water and acetone. The solid was then dried at a pressure of 0.05 mbar at 100° C. for 5 hours to produce solid C.

Elemental analysis of solid C gave the following results: Ti, 35.6%; P, 4.8%; S, 6.5. The Ti/P ratio was 4.8 and the S/P ratio was 0.8.

The phosphorous-31 NMR spectrum of solid C (see FIG. 1) carried out using a 300 MHz Bruker Avance apparatus showed a broad peak at 25.1 ppm corresponding to phosphonate groups bonded to titanium atoms; the carbon-13 NMR spectrum of solid B, carried out using a 300 MHz Bruker Avance apparatus, showed three peaks at 26.2 ppm, 19.9 ppm and 53.1 ppm, corresponding to three methylene groups in the P—$CH_2$—$CH_2$—$CH_2$—S concatenation.

The invention claimed is:

1. A material comprising groups containing sulfur and phosphorous bonded together by a hydrocarbon chain and bonded via said phosphorous and via oxygen atoms to a metal oxide of one or more elements M, said materials comprising M-O-M' groups, M' representing an element of a metal oxide identical to or different from M, wherein in said material the ratio of said element M to the phosphorous is about 0.5:1 to about 500:1, and each phosphorous atom of the phosphorous-containing groups forms at least one P—O-M group and/or P—O-M' group, said material being prepared by gel formation.

2. A material according to claim 1, in which M and M' represent the same element.

3. A material according to claim 2, wherein M and M' represent Ti.

4. A material according to claim 1, wherein the ratio of M to phosphorous is about 3.4:1 to 500:1.

5. A process for preparing a material according to claim 1, in which at least one halogenated derivative of the formula $M(Hal)_z$ or at least one alkoxylated derivative of the formula $M(OR')_z$, wherein z is equal to the valency of the element M, Hal is a halogen atom, R' is a hydrocarbon group, or at least one compound of element M selected from the group consisting of carboxylates, sulphates, nitrates, hydroxides and oxychlorides, is brought into contact with at least one solvent solution of at least one phosphorous-containing compound of formula I

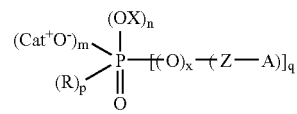

wherein the sum m+n+p+q is equal to 3, m=0, 1 or 2, q=0, 1 or 2, x=0 or 1, p=0, 1 or 2, R is a hydrocarbon group, X is a hydrocarbon group or a group of the formula SiR''$_3$ where R'' is a hydrocarbon group, Z is a hydrocarbon group optionally comprising heteroatoms, Cat$^+$ is a monovalent cation, and A is a sulfur-containing group or a reactive group that can be transformed into a sulfur-containing group.

6. A process according to claim 5, in which an alkoxylated derivative of the formula $M(OR')_z$, wherein R' is an alkyl group containing 1 to 12 carbon atoms, is brought into contact with a solution in a solvent of a phosphorous-containing compound of formula I wherein Cat$^+$ is a proton H+, R is an alkyl group containing 1 to 18 carbon atoms or an aryl group containing 6 to 18 carbon atoms or an alkyl-aryl group containing 7 to 24 carbon atoms, X is a group of the formula SiR''$_3$, wherein R'' is a hydrocarbon group, Z is (i) a saturated or unsaturated divalent alkyl group containing 1 to 18 carbon atoms, (ii) a divalent aryl group containing 6 to 18 carbon atoms or (iii) a divalent alkyl-aryl or aryl-alkyl group containing 7 to 24 carbon atoms and A is a thiol group, a derivative thereof, a suiphonic acid group or a derivative thereof.

7. A process according to claim 5, in which the phosphorous-containing compound of formula I is a compound in which m=2, q=1 and n=p=zero.

8. A process according to claim 5, in which the phosphorous-containing compound of formula I is a compound in which n=2, q=1 and m=p=zero.

9. A process according to claim 5, in which the phosphorous-containing compound of formula I is a compound in which Z is a saturated divalent alkylene compound group containing 1 to 18 carbon atoms, a divalent arylene group containing 6 to 18 carbon atoms, or a divalent alkyl-arylene or arylalkylene group containing 7 to 24 carbon atoms.

10. A process according to claim 5, in which the solvent for the phosphorous-containing compound of formula I, is tetrahydrofuran, dimethylsulphoxide dichloromethane or water.

11. A material produced according to the process of claim 5.

12. A material according to claim 1, in which M and M' represent an element from groups 3, 4, 5, 6, 7, 8, 9, 10, 11, 12, 13, 14, the lanthanides or the actinides of the periodic table.

13. A material according to claim 1, in which M and M' are titanium, zirconium, iron, aluminium, silicon or tin.

14. A material according to claim 1, in which M and M' are by titanium, zirconium or aluminium.

15. A material according to claim 1, in which the sulfur-containing groups are thiol groups, derivatives thereof, acid sulphonic groups or derivatives thereof.

16. A material according to claim 14, in which the sulfur-containing groups are thiol groups, derivatives thereof, acid sulphonic groups, or derivatives thereof.

17. A process according to claim 6, wherein R' is an alkyl group containing 1–6 carbon atoms.

18. A process according to claim 6, in which the phosphorous-containing compound of formula I is a compound in which m=2, q=1 and n=p=zero.

19. A process according to claim 6, in which the phosphorous-containing compound of formula I is a compound in which n=2, q=1 and m=p=zero.

20. A material produced according to the process of claim 6.

21. A material produced according to the process of claim 7.

22. A material produced according to the process of claim 8.

23. A process according to claim 9, wherein Z is a $(CH_2)_{1-6}$ group.

24. A material produced according to the process of claim 9.

25. A material produced according to the process of claim 10.

26. A material according to claim 11, wherein M and M' represent Ti.

27. A material comprising groups containing sulfur and phosphorous bonded together by a hydrocarbon chain and bonded via phosphorous and oxygen atoms to a metal oxide of one or more elements M, said materials comprising M-O-M' groups, M' representing an element of a metal oxide identical to or different from M, the ratio of said element M to the phosphorous being about 0.5:1 to about 500:1, each phosphorous atom of the phosphorous-containing groups forming at least one P—O-M group and/or P—O-M' group, said material being prepared by gel formation in which at least one halogenated derivative with formula $M(Hal)_z$ or at least one alkoxylated derivative with formula $M(OR')_z$, where z is equal to the valence of the element M, Hal is a halogen atom, R' is a hydrocarbon group, or at least one carboxylate, sulfate, nitrate, hydroxide or oxychloride of element M is brought into contact with at least one solution in a solvent of at least one phosphorous-containing compound with formula I

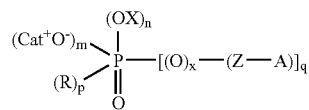

I where the sum m+n+p+q is equal to 3, m=0, 1 or 2, q=0, 1 or 2, x=0 or 1, p=0, 1 or 2, R is a hydrocarbon group, X is a hydrocarbon group or a group with formula $SiR''_3$ where R'' is a hydrocarbon group, Z is a hydrocarbon group optionally comprising heteroatoms, Cat+ is a monovalent cation and A is a sulfur-containing group or a reactive group that can be transformed into a sulfur-containing group.

* * * * *

UNITED STATES PATENT AND TRADEMARK OFFICE
CERTIFICATE OF CORRECTION

PATENT NO.         : 7,160,836 B2                                       Page 1 of 1
APPLICATION NO.    : 11/200038
DATED              : January 9, 2007
INVENTOR(S)        : Alain Forestiere It is certified that error appears in the above-identified patent and that said Letters Patent is hereby corrected as shown below:

On the Title page Item (73), Assignee: line 1, reads "Francois" should read -- Francais --
On the Title page Item (73), Assignee: line 2, reads "Reuil-Malmaison" should read
-- Reuil Malmaison --
Column 6, line 49, reads "H+," should read -- $H^+$, --
Column 6, line 57, reads "suiphonic" should read -- sulphonic --
Column 7, line 6, reads "formula I, is" should read -- formula I is --
Column 7, line 7, reads "dimethylsulphoxide dichloromethane" should read
-- dimethylsulphoxide, dichloromethane --
Column 7, line 16, reads "aluminium," should read -- aluminum, --
Column 7, line 18, reads "are by titanium," should read -- are titanium, --
Column 7, line 18, reads "aluminium." should read -- aluminum. --
Column 8, line 37, reads "Cat+is" should read -- $Cat^+$ is --

Signed and Sealed this

Third Day of February, 2009

JOHN DOLL
*Acting Director of the United States Patent and Trademark Office*